(12) United States Patent
Asnes

(10) Patent No.: US 12,369,003 B2
(45) Date of Patent: *Jul. 22, 2025

(54) ENVIRONMENTAL CLASSIFICATION CONTROLLED OUTPUT LEVEL IN BONE CONDUCTION DEVICES

(71) Applicant: Cochlear Limited, Macquarie University (AU)

(72) Inventor: Kristian Gunnar Asnes, Molndal (SE)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/464,698

(22) Filed: Sep. 11, 2023

(65) Prior Publication Data

US 2024/0048923 A1 Feb. 8, 2024

Related U.S. Application Data

(63) Continuation of application No. 17/273,158, filed as application No. PCT/IB2019/061017 on Dec. 18, 2019, now Pat. No. 11,785,402.

(60) Provisional application No. 62/782,399, filed on Dec. 20, 2018.

(51) Int. Cl.
*H04R 25/00* (2006.01)
*G10L 25/84* (2013.01)

(52) U.S. Cl.
CPC ............ *H04R 25/606* (2013.01); *G10L 25/84* (2013.01); *H04R 25/30* (2013.01); *H04R 2460/13* (2013.01)

(58) Field of Classification Search
CPC ...... H04R 25/00; H04R 25/30; H04R 25/606; H04R 2460/13
See application file for complete search history.

(56) References Cited

U.S. PATENT DOCUMENTS

| 6,236,731 | B1 | 5/2001 | Brennan et al. |
| 11,785,402 | B2 * | 10/2023 | Asnes .................... H04R 25/30 381/326 |
| 2010/0016922 | A1 | 1/2010 | Daly |
| 2012/0109297 | A1 | 5/2012 | Van Den Heuvel |
| 2012/0253104 | A1 | 10/2012 | Andersson et al. |
| 2018/0140838 | A1 | 5/2018 | Smith |
| 2021/0058713 | A1 | 2/2021 | Jensen et al. |

FOREIGN PATENT DOCUMENTS

| EP | 2758956 A1 | 7/2014 |
| KR | 10-2018-0090227 A | 8/2018 |

OTHER PUBLICATIONS

European Communication pursuant to Article 94(3) EPC in counterpart European Application No. 19 898 533-1207, mailed Jun. 28, 2024, 7 pages.

(Continued)

*Primary Examiner* — Suhan Ni
(74) *Attorney, Agent, or Firm* — Edell, Shapiro & Finnan, LLC

(57) ABSTRACT

A bone conduction device is configured to classify received sound signals (sounds) into one or more sound categories/classes (i.e., determine the input signal type). The bone conduction device is configured to dynamically set a maximum force output (MFO) of the bone conduction device at least based on the sound class of the sound signals.

18 Claims, 8 Drawing Sheets

(56) References Cited

OTHER PUBLICATIONS

Extended European Search Report in counterpart European Application No. 19898533.5-1207, mailed Jul. 15, 2022, 10 pages.
Breitholz Fredrik: "Maximum Power Output and Maximum Force Output Available to Baha Patients", Audiology Online, Aug. 20, 2018 {Aug. 20, 2018), XP055940239, Retrieved from the Internet: URL:https://www.audiologyonline.com/interviews/maximum-power-output-and-force-23637.
International Search Report and Written Opinion in counterpart International Application No. PCT/182019/061017, mailed Jul. 3, 2020, 9 pages.

\* cited by examiner

FIG. 3A

| SOUND CLASS | AVERAGE MFO (dB rel. 1μN) |
|---|---|
| SPEECH | 120 |
| NOISE | 120 |
| SPEECH + NOISE | 125 |
| WIND | 120 |
| MUSIC | 120 |
| QUIET | 120 |

FIG. 3B

| SOUND CLASS | AVERAGE MFO (dB rel. 1μN) |
|---|---|
| SPEECH | 120 |
| NOISE | 120 |
| SPEECH + NOISE | 125 |
| WIND | 120 |
| MUSIC | 125 |
| QUIET | 120 |

FIG. 3C

| SOUND CLASS | AVERAGE MFO (dB rel. 1μN) |
|---|---|
| SPEECH | 120 |
| NOISE | 115 |
| SPEECH + NOISE | 125 |
| WIND | 115 |
| MUSIC | 122 |
| QUIET | 115 |

FIG. 4A

| SOUND CLASS | SNR THRESHOLD (dB) | AVERAGE MFO (dB rel. 1 μN) |
|---|---|---|
| SPEECH | X | 120 |
| NOISE | X | 120 |
| SPEECH + NOISE | 6 dB | 125 |
| WIND | X | 120 |
| MUSIC | X | 120 |
| QUIET | X | 120 |

FIG. 4B

| SOUND CLASS | SNR THRESHOLD (dB) | AVERAGE MFO (dB rel. 1 μN) |
|---|---|---|
| SPEECH | X | 120 |
| NOISE | X | 120 |
| SPEECH + NOISE | 6 dB | 125 |
| WIND | X | 120 |
| MUSIC | 6 dB | 125 |
| QUIET | X | 120 |

FIG. 4C

| SOUND CLASS | SNR THRESHOLD (dB) | AVERAGE MFO (dB rel. 1 μN) |
|---|---|---|
| SPEECH | 6 dB | 120 |
| NOISE | X | 115 |
| SPEECH + NOISE | 10 dB | 125 |
| WIND | X | 115 |
| MUSIC | 9 dB | 122 |
| QUIET | X | 115 |

ENVIRONMENTAL CLASSIFICATION CONTROLLED OUTPUT LEVEL IN BONE CONDUCTION DEVICES

BACKGROUND

Field of the Invention

The present invention relates generally to bone conduction devices.

Related Art

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient to bypass the mechanisms of the ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, which rely primarily on the principles of air conduction, certain types of hearing prostheses, commonly referred to as bone conduction devices, convert a received sound into vibrations. The vibrations are transferred through the skull to the cochlea causing generation of nerve impulses, which result in the perception of the received sound. Bone conduction devices are suitable to treat a variety of types of hearing loss and may be suitable for individuals who cannot derive sufficient benefit from acoustic hearing aids, cochlear implants, etc., or for individuals who suffer from stuttering problem.

SUMMARY

In one aspect, a method is provided. The method comprises: receiving sound signals at a bone conduction device; determining a sound class of the sound signals; and dynamically setting a maximum force output (MFO) of the bone conduction device at least based on the sound class of the sound signals.

In another aspect, a method is provided. The method comprises: receiving sound signals at a bone conduction device located in an acoustic environment, wherein the bone conduction device comprises an actuator and at least one battery; assessing, based on the sound signals, the acoustic environment of the bone conduction device; determining, based at least in part on the acoustic environment of the bone conduction device, an instantaneous amount of power that is available from the at least one battery to other components of the bone conduction device; generating, based on the sound signals and the instantaneous amount of power that is available from the at least one battery to other components of the bone conduction device, electrical signals for use in driving the actuator for delivery of mechanical force to tissue of a user of the bone conduction device; and driving the actuator with the electrical signals.

In another aspect, a bone conduction device is provided. The bone conduction device comprises: one or more sound input elements configured to receive sound signals; at least one battery; an actuator; an environmental classifier configured to determine a sound class of the sound signals; a sound processing module and amplifier configured to convert the sound signals into one or more output signals for use in driving the actuator; and a controller configured to set, based on the sound class of the sound signals, a maximum peak battery power available to the sound processing module and amplifier when generating the output signals.

BRIEF DESCRIPTION OF THE DRAWINGS

Embodiments of the present invention are described herein in conjunction with the accompanying drawings, in which:

FIGS. 3A-3C are tables illustrating example average maximum force outputs (MFOs) for bone conduction devices, in accordance with certain embodiments presented herein;

FIGS. 4A-4C are tables illustrating example average MFOs for bone conduction devices, in accordance with certain embodiments presented herein;

DETAILED DESCRIPTION

Presented herein are techniques in which a bone conduction device is configured to classify received sound signals (sounds) into one or more sound categories/classes (i.e., determine the input signal type). The bone conduction device is configured to dynamically set a maximum force output (MFO) of the bone conduction device at least based on the sound class of the sound signals.

Figure 1A:
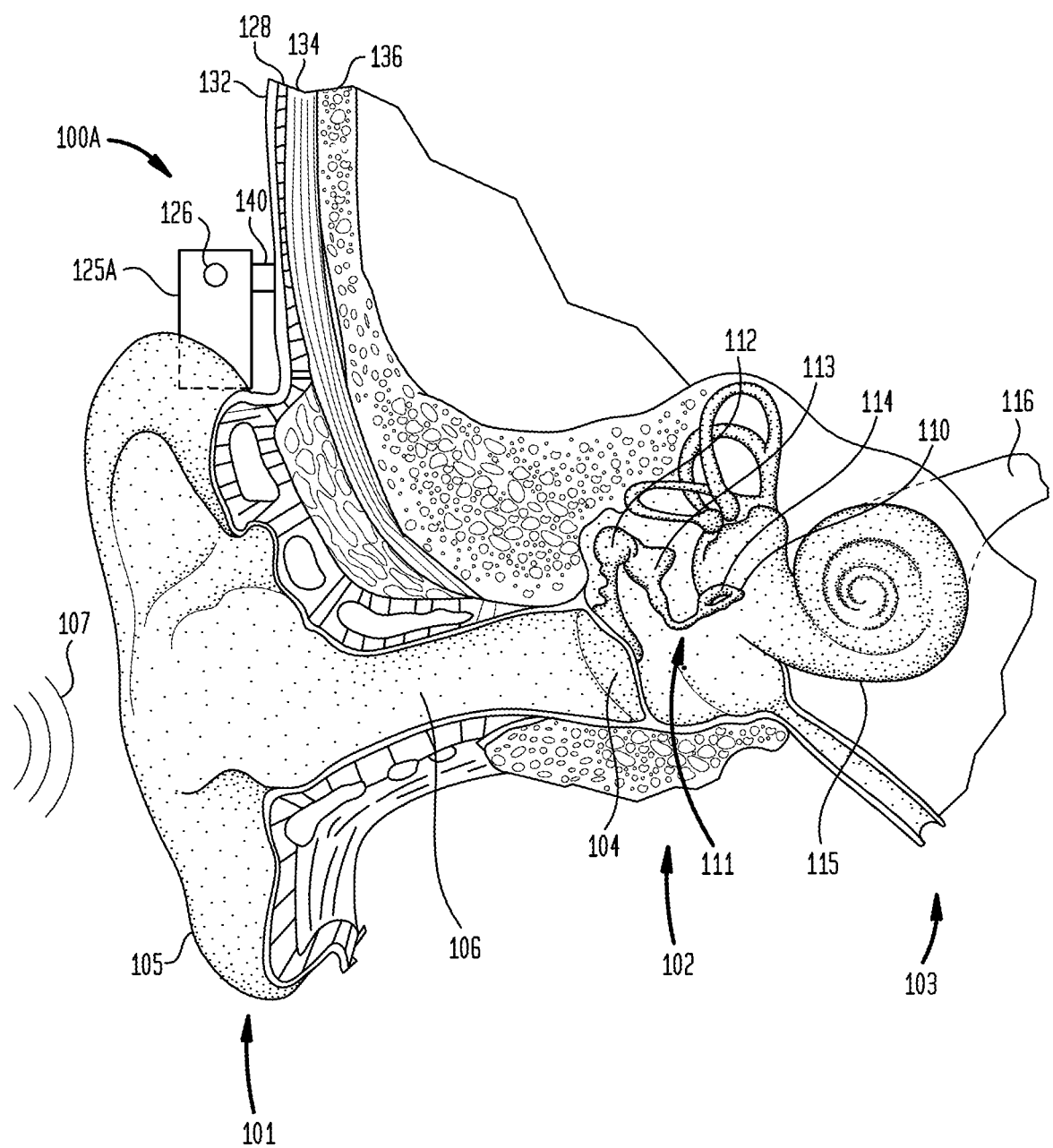
FIG. 1A is a perspective view of an exemplary bone conduction device in which at least some embodiments presented herein can be implemented.

FIG. 1A is a perspective view of a bone conduction device 100A in which certain embodiments presented herein may be implemented. As shown, the recipient has an outer ear 101, a middle ear 102 and an inner ear 103. Elements of outer ear 101, middle ear 102 and inner ear 103 are described below, followed by a description of bone conduction device 100A.

In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. The ossicles 111 of middle ear 102 serve to filter and amplify acoustic wave 107, causing oval window 110 to vibrate. Such vibration sets up waves of fluid motion within cochlea 139. Such fluid motion, in turn, activates hair cells (not shown) that line the inside of cochlea 139. Activation of the hair cells causes appropriate nerve impulses to be transferred through the spiral ganglion cells and auditory nerve 116 to the brain (not shown), where they are perceived as sound.

FIG. 1A also illustrates the positioning of bone conduction device 100A relative to outer ear 101, middle ear 102 and inner ear 103 of a recipient of device 100. As shown, bone conduction device 100 is positioned behind outer ear 101 of the recipient and comprises one or more sound input devices 126 to receive sound signals. The sound input elements may comprise, for example, a microphone, telecoil, etc. In an exemplary embodiment, sound input element 126 is a microphone located, for example, on or in bone conduction device 100A. Alternatively, the microphone 126 could be located on a cable extending from bone conduction device 100A, physically separated from the bone conduction device (e.g., an in-the-ear microphone in wireless communication with the bone conduction device), etc.

In an exemplary embodiment, bone conduction device 100A is an operationally removable component configured to be releasably coupled to a bone conduction implant (not shown in FIG. 1A). That is, the bone conduction device 100A can be attached/detached to/from the bone conduction implant by the recipient (or other user) during normal use of the bone conduction device 100A. Such releasable coupling is accomplished via a coupling assembly 140 that is configured to mechanically mate with the bone conduction implant.

The bone conduction device 100A includes a housing 125A in which a sound processing module, an actuator/transducer, amplifier, controller, and/or various other electronic circuits/devices are positioned. The actuator may comprise, for example, a vibrating electromagnetic actuator, a vibrating piezoelectric actuator, or another type of actuator. In operation, the microphone 126 (e.g., microphone) converts received sound signals into electrical signals. These electrical signals are processed by the sound processing module. The sound processing module generates control signals which cause the actuator to vibrate. In other words, the actuator converts the electrical signals into mechanical motion to impart vibrations to the recipient's skull. As such, the bone conduction device 100A is sometimes referred to as a "vibrator unit" or "vibrator," since it generates vibration for delivery to the skull of the recipient.

As shown in FIG. 1A, the bone conduction device 100A further includes a coupling assembly 140 configured to be removably attached to the bone conduction implant (sometimes referred to as an anchor system and/or a fixation system) implanted in the recipient. In the embodiment of FIG. 1A, the bone conduction implant includes a percutaneous abutment attached to a bone fixture via a screw, where the bone fixture is fixed to the recipient's skull bone 136. The abutment extends from the bone fixture which is screwed into bone 136, through muscle 134, fat 128 and skin 232 so that the coupling assembly 140 may be attached thereto. Such a percutaneous abutment provides an attachment location for the coupling assembly that facilitates efficient transmission of mechanical force (vibration) generated by the bone conduction device 100A. Due to the use of the percutaneous abutment, the bone conduction device 100A is sometimes referred to as a "percutaneous bone conduction device."

Figure 1B:
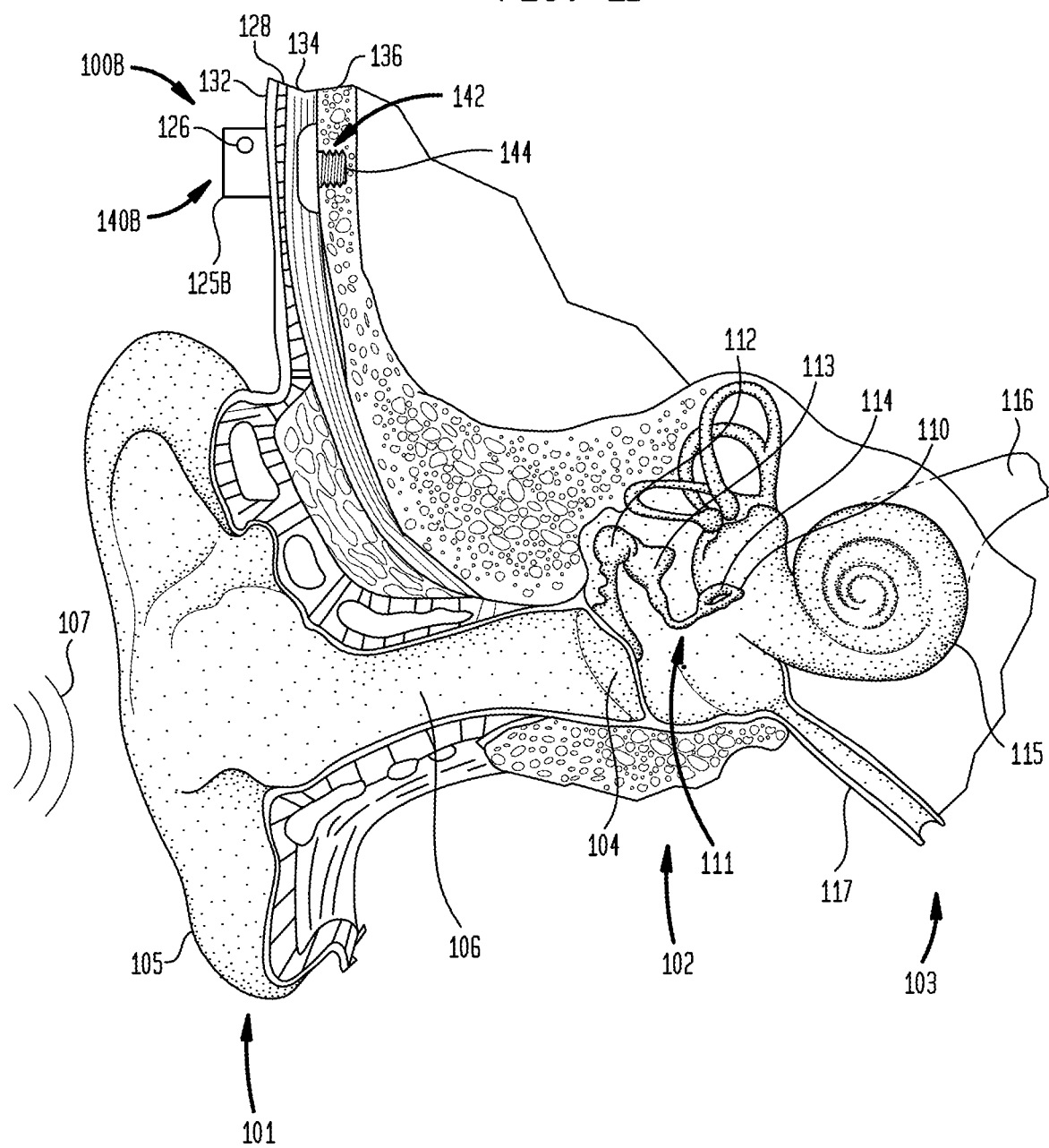
FIG. 1B is a perspective view of an alternate exemplary bone conduction device in which at least some embodiments presented herein can be implemented.

Although FIG. 1A illustrates a percutaneous bone conduction device 100A, it is to be appreciated that certain aspects presented herein may be utilized with other types of bone conduction devices. For example, FIG. 1B is a perspective view of a "transcutaneous bone conduction device" 100B in which embodiments presented herein can be implemented. As described further below, a transcutaneous bone conduction device is a bone conduction device that does not use a percutaneous abutment. Instead, the transcutaneous bone conduction device is held against the skin via a magnetic coupling (e.g., magnetic material and/or magnets being implanted in the recipient and the vibrator having a magnet and/or magnetic material to complete the magnetic circuit, thereby coupling the vibrator to the recipient).

More specifically, FIG. 1B also illustrates the positioning of transcutaneous bone conduction device 100B relative to outer ear 101, middle ear 102 and inner ear 103 of a recipient of device 100. As shown, bone conduction device 100B is positioned behind outer ear 101 of the recipient and comprises a housing 125B having a microphone 126 positioned therein or thereon. Disposed in housing 125B is a magnetic component, a sound processing module, an actuator (e.g., electromagnetic actuator, piezoelectric actuator, etc.), amplifier, and/or various other electronic circuits/devices are positioned. Similar to bone conduction device 100A of FIG. 1A, in FIG. 1B the microphone 126 (e.g., microphone) converts received sound signals into electrical signals. These electrical signals are processed by the sound processing module. The sound processing module generates control signals which cause the actuator to vibrate. In other words, the actuator converts the electrical signals into mechanical motion to impart vibrations to the recipient's skull.

In accordance with the embodiment of FIG. 1B, a fixation system 144 may be used to secure an implantable component 142 to skull 136. As described below, fixation system 144 may be a bone screw fixed to skull 136, and also attached to implantable component 142.

In the arrangement of FIG. 1B, the bone conduction device 100B is a passive transcutaneous bone conduction device. That is, no active components, such as the actuator, are implanted beneath the recipient's skin 132. Instead, the active actuator is located in bone conduction device 140B and the implantable component 142 includes a magnetic plate. The magnetic plate of the implantable component 142 vibrates in response to vibrations transmitted through the skin, mechanically and/or via a magnetic field, that are generated by the magnetic component (plate) in the bone conduction device 100B.

Collectively, FIGS. 1A and 1B illustrate two arrangements of bone conduction devices in which embodiments presented herein may be implemented. However, it is to be appreciated that the embodiments shown in FIGS. 1A and 1B are merely illustrative and that the techniques presented herein may be used in other arrangements. For example, the techniques presented herein could also or alternatively be implemented with "active transcutaneous bone conduction devices" where the actuator is implanted within the recipient (e.g., in implantable component 142). In such arrangements, the a sound processing module may be disposed in an external component and electrical signals representative of the processed sound signals are transcutaneously sent to the implantable component for use in driving the actuator and, as such, generating vibration for delivery to the recipient.

Figure 2:
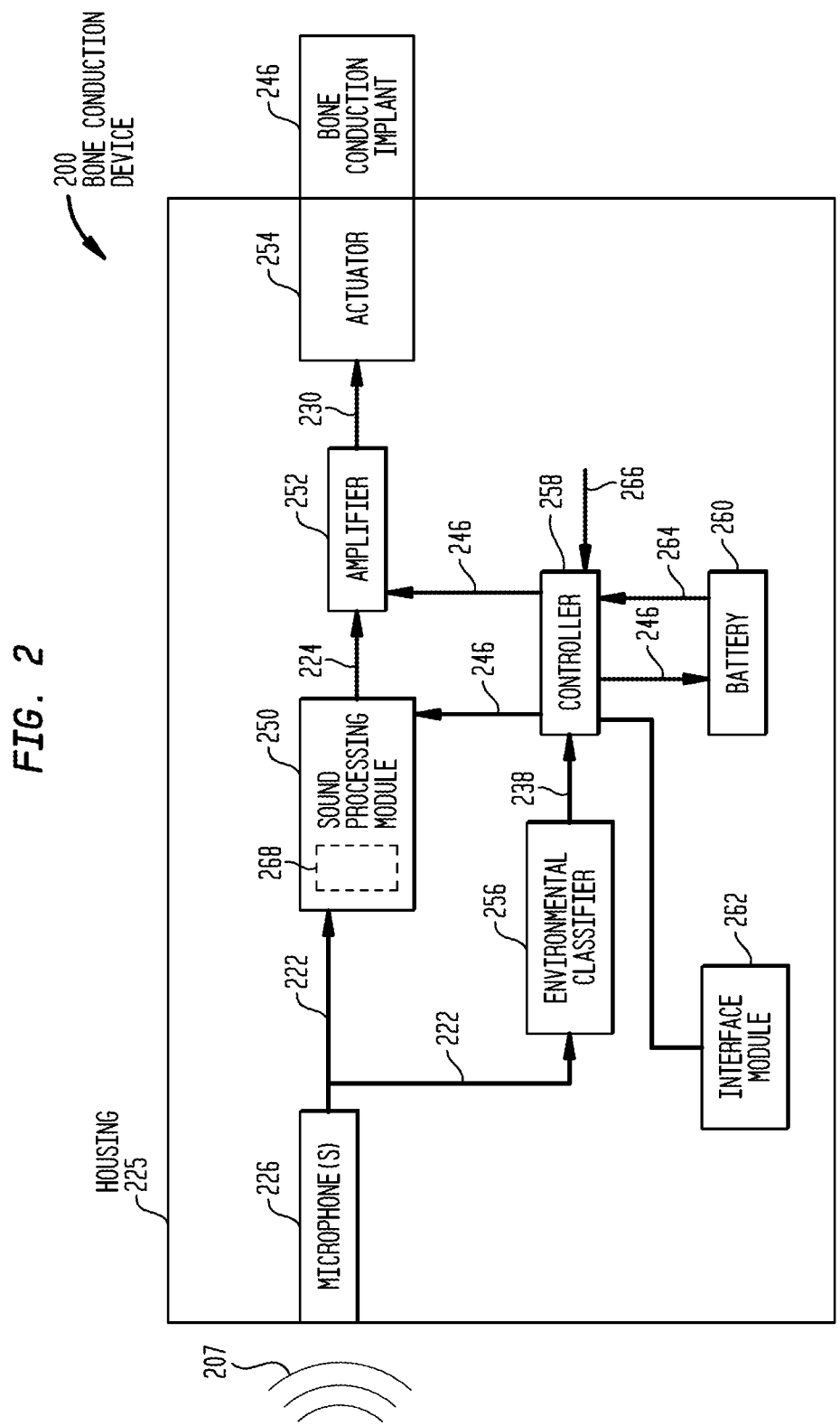
FIG. 2 is a functional block diagram of an embodiment of a bone conduction device, in accordance certain embodiments presented herein.

In general, FIGS. 1A and 1B illustrate that bone conduction devices are configured to receive and process sound signals, and to use those sound signals to generate vibrations for delivery to the recipient. FIGS. 1A and 1B correspond to percutaneous and transcutaneous mechanisms, respectively, for delivery of the vibrations to the recipient. FIG. 2 is a functional block diagram illustrating further details regarding how sound signals are used to generate vibrations for delivery to the recipient, in accordance with certain embodiments presented herein.

More specifically, shown in FIG. 2 is a bone conduction device 200 mechanically or magnetically coupled to a bone conduction implant 246 (representing a percutaneous or transcutaneous vibration delivery mechanism). Bone conduction device 200 comprises a housing 225 and one or more sound input devices, namely microphones 226, disposed in or on the housing 225. The bone conduction device 200 may include additional sound input devices which, for ease of illustration, have been omitted from FIG. 2.

The bone conduction device 200 also comprises a sound processing module 250, an amplifier 252, an actuator 254, an environmental classifier 256, a controller (control circuit) 258, at least one battery 260, and an interface module 262. In operation, the microphone(s) 226 are configured to receive sound signals (sound) 207, and to convert the received sound 207 into electrical signals 222. If other sound input devices are present, the sound 207 could also or alternatively may be received by as an electrical signal.

As shown in FIG. 2A, electrical signals 222 are output by microphone 226 to a sound processing module 250. The sound processing module 250 is configured to convert the electrical signals 222 into adjusted/processed electrical signals 224. That is, the sound processing module 250 is configured to apply one or more processing operations (e.g., filtering, noise reduction, automatic gain control/adjustment, loudness compression, etc.) to the electrical signals 222. In certain embodiments, the sound processing module 250 may include a digital signal processor.

The processed electrical signals 224 are provided to the amplifier 252. The amplifier 252 amplifies (i.e., increases the time-varying voltage or current) the processed electrical signals 224 to generate amplified output signals 230. The amplified output signals 230 are then used to drive (activate) the actuator 254 which, in turn, generates corresponding vibrations. That is, using the amplified output signals 230, the actuator 254 generates a mechanical output force that is delivered to the skull of the recipient via bone conduction implant 246. Delivery of this output force causes one or more of motion or vibration of the recipient's skull, thereby activating the hair cells in the cochlea via cochlea fluid motion and, in turn, evoking perception by the recipient of the received sound signals 207.

As noted, bone conduction device 200 comprises at least one battery 260. The at least one battery 260 provides electrical power to the various components of bone conduction device 200. For ease of illustration, battery 260 has been shown connected only to controller 258. However, it should be appreciated that battery 260 may be used to supply power to any electrically powered circuits/components of bone conduction device 200, including sound processing module 250, amplifier 252, actuator 254, etc.

Bone conduction device 200 further includes the interface module 262 that allows the recipient or other user to interact with device 200. For example, interface module 262 may allow the recipient to adjust the volume, alter the speech processing strategies, power on/off the device, etc. Again, for ease of illustration, interface module 262 has been shown connected only to controller 258.

In the embodiment illustrated in FIG. 2, the components (e.g., microphone 226, actuator 254, etc.) have all been shown as integrated into a single housing, referred to as housing 225. However, it should be appreciated that in certain embodiments of the present invention, one or more of the illustrated components may be housed in separate or different housings. Similarly, it should also be appreciated that in such embodiments, direct connections between the various modules and devices are not necessary and that the components may communicate, for example, via wireless connections.

A bone conduction device, such as bone conduction device 200, operates in accordance with a number of different parameters. One such parameter is the Maximum Force Output (MFO) of the bone conduction device 200. As used herein, MFO refers to the maximum allowable output that the bone conduction device 200 can produce For bone conduction devices, MFO is measured in dB relative to one micro Newton of force (dB rel. 1 μN). For ease of description, the techniques presented herein will be described with reference to the MFO of bone conduction device 200.

It is to be understand that, as used herein, the MFO is specifically tied to the peak power/energy that can be drawn from the battery/batteries of the bone conduction device at a given time. That is, the MFO specifically corresponds to the instantaneous amount of power that is available, from the device battery/batteries, to other components of the bone conduction device when generating vibration for delivery to the recipient. Therefore, as described further below, dynamically increasing the MFO refers to dynamically increasing the amount of battery power that is available to one or more components of the bone conduction device, when generating vibration for delivery to the recipient. Accordingly, when more battery power is made available, the output(s) generated by the bone conduction device may be higher.

It is also to be understood that the MFO refers to the maximum "allowable" output that a bone conduction device produces. The MFO, even when increased as described further below, would still be below the maximum capabilities of the device components themselves (i.e., MFO does refer to the levels/points at which components of the device will begin to fail, but is set below such failure levels).

Moreover, it is to be understood that the MFO of a bone conduction device is separate and distinct from any gain adjustments in the bone conduction device. More specifically, the sound processing modules of bone conduction devices may include dynamic or automatic gain control, which operates as regulating circuit for the amplifier(s). The purpose of the gain control is to maintain a suitable signal amplitude at its output, despite variation of the signal amplitude at the input. For example, in one arrangement, the average or peak output signal level is used to dynamically adjust the gain of the amplifiers, enabling the circuit to work satisfactorily with a greater range of input signal levels. Although these gain adjustments may affect the levels of the outputs generated by the bone conduction device, such adjustments are not related to the allowable maximum levels of battery power that would be available for use. Instead, any gain adjustments are performed within the framework of whatever MFO is currently set for a bone conduction device (i.e., the MFO acts as a control for the gain adjustments). In one example, increasing the MFO of a bone conduction device could potentially enable the automatic gain control to increase the output signals levels, although the inverse is not true (i.e., increasing the gain does not increase, nor does it affect, the MFO of the bone conduction device).

MFO is important as it sets the dynamic range that a bone conduction device can provide to a recipient. There are two types of dynamic range, namely that of the amplifier 252 and that of recipient's hearing. With amplifier 252, the dynamic range is defined as the difference between the smallest amplified intensity and the loudest output of the amplifier. For human hearing, the dynamic range is defined as the difference between the softest sound heard and sounds that are uncomfortably loud.

Normal hearing individuals can have dynamic ranges of 100 dB or more, meaning the softest sound they can hear and the point at which sound becomes uncomfortably loud can range up to 100 dB. Sensorineural hearing loss and conductive hearing loss may affect this dynamic range in different ways. For example, with sensorineural hearing loss, the recipient's thresholds are increased (meaning sound has to be louder before they can hear it), but their loudness tolerance is either the same or can be decreased, leading to an overall reduction in dynamic range. This must be addressed when fitting amplification, usually by compressing the amplifier's dynamic range to accommodate the patient's impaired range of hearing. With conductive hearing loss, the recipient's thresholds are increased, as it is with sensorineural hearing loss, but their loudness tolerance is also increased, mostly preserving the dynamic range.

Therefore, while a recipient with sensorineural hearing loss may require more gain for soft sounds and less or no gain for loud sounds, a recipient with conductive hearing loss will require similar gain for soft, moderate and loud sounds (i.e., linear amplification). This means someone with a conductive component to their hearing loss may require a much higher output than someone with sensorineural hearing loss and therefore a bone conduction device with a large dynamic range.

Generally, the need for additional power in a normal hearing aid (i.e., for sensorineural loss) is relatively small because the hearing aid only drives the tympanic membrane. In contrast, .due to the operational nature of bone conduction devices (i.e., inducing vibration of a recipient's heavy skull) and the need to keep the devices reasonably small, is more difficult to achieve high output levels in bone conduction devices (i.e., vibrating the whole skull is much more energy demanding than simply driving the tympanic membrane). Additionally, when a bone conduction device operates at/with a higher MFO, the result is high power consumption, when compared to operation at a lower MFO.

Bone conduction devices generally operate using power supplied by at least one battery disposed in the device. Bone conduction devices may traditionally been powered by disposable batteries, such as Zinc-air batteries, which generally have a limited peak (instantaneous) power capability. Therefore, operation of bone conduction devices having disposable batteries at a higher MFO presents a risk for an unexpected shutdown of the bone conduction device (i.e., because more instantaneous power is drawn from the battery). For hearing impaired recipients, unexpected shutdowns are not only problematic, but also potentially dangerous.

More recently, rechargeable batteries, such as lithium-ion (Li-ion) batteries, have been proposed for use in bone conduction devices. While a disposable battery is typically able to power a bone conduction device for several days, most rechargeable batteries have a limited total energy per volume which results in a shorter operational life when compared to disposable batteries. Despite the limited total energy per volume, and the battery size restraints associated with bone conduction devices, the expectation is that a rechargeable battery should be able to power the bone conduction device for a full day of use by the recipient (e.g., 14 hours, 16 hours, etc.). As noted, operation of bone conduction devices with a higher MFO increases the power consumption of the device which, in turn, can further shorten the operational life of bone conduction devices with rechargeable batteries. With rechargeable batteries, this is particularly problematic since the reduced operational life could leave the recipient without an operational bone conduction device during the day.

In summary, operation of bone conduction devices with a higher MFO can improve the recipient's sound perception. However, there is a significant power consumption cost associated with operating a bone conduction device at such high output levels, which could cause unexpected shutdowns or decrease the operating life of the device. As a result, conventional bone conduction devices may simply limit the bone conduction device output level to a pre-determined/fixed MFO (e.g., determined at the time of fitting) that ensures an acceptable battery life and/or that prevents unexpected shutdown. However, by artificially reducing the MFO of the bone conduction device, such conventional bone conduction devices inherently limit the hearing performance that can be achieved by the bone conduction device. Accordingly, presented herein are techniques that balance the improved hearing performance provided by high output levels (i.e., operation at a higher MPO) with power consumption/battery life limitations. In particular, the techniques presented herein provide a bone conduction devices with a dynamic MFO adjustments, where the MFO of the bone conduction device can be set, in real-time, based on parameters of the received sound signals, such as the sound class/environment associated with the sound signals.

More specifically, returning to the specific example of FIG. 2, the bone conduction device 200 includes an environmental classification module (environmental classifier) 256. As shown, the environmental classifier 256 receives the electrical signals 222 output by the microphone(s) 226. Using these electrical signals, the environmental classifier 256 is configured to evaluate/analyze the received sound signals (sounds) 207 and determine the sound class/category/environment of the sounds. That is, the environmental classifier 256 is configured to use the received sounds to "classify" the ambient sound environment and/or the sounds into one or more sound categories (i.e., determine the input signal type). The sound class or environment may include, but are not limited to, "Speech" (e.g., the sound signals include primarily speech signals), "Noise" (e.g., the sound signals include primarily noise signals), "Speech+Noise" (e.g., both speech and noise are present in the sound signals), "Wind" (e.g., e.g., the sound signals include primarily wind signals), "Music" (e.g., the sound signals include primarily music signals), and "Quiet" (e.g., the sound signals include minimal speech or noise signals). The environmental classifier 256 may also estimate the signal-to-noise ratio (SNR) of the sounds. In one example, the environmental classifier 256 generates sound classification information/data 238. The sound classification data 238 represents the sound class of the sound signals and, in certain examples, the SNR of the sound signals.

As noted, bone conduction device 200 also comprises controller 258. The controller 258 is configured to use the sound classification data 238 (e.g., indicating the sound class of the sound signals) to determine whether the bone conduction device 200 is in a listening environment in which the recipient could benefit from a higher output. In such environments, the controller 258 is configured to dynamically adjust operation of the bone conduction device 200 to temporarily increase the MFO of the bone conduction device (i.e., the controller 258 is configured to set, based on the sound class of the sound signals, a maximum peak battery power available to the sound processing module and amplifier when generating the amplified output signals 230).

That is, certain sound classes may benefit from the generation of vibrations with using a higher MFO (e.g., Music, Speech, speech-in-noise), while others (e.g., Wind, Noise, Quiet) may not. For example, in a "Quiet" environment, there would be no effect of adjusting the MFO since the sound levels are already low and there would be no audible improvements or any power consumption effect. If the controller 258 determines that the sound class of the sound signals matches a sound class that can benefit from a higher MFO, then the controller 258 can make corresponding adjustments to various parameters, settings, operations, etc. of the bone conduction device to dynamically achieve the higher MFO. That is, based on the sound class of the received sound signals, the controller 258 enables, in real-time, components of the bone conduction device 200 (e.g., sound processing module 250, amplifier 252, etc.) to temporarily draw/consume an increased amount of peak power/energy from the at least one battery 260 while generating amplified output signals 230 and, accordingly, the vibration for delivery to the recipient. Therefore, dynamically increasing the MFO refers to dynamically increasing the amount of battery power that is available to one or more components of the bone conduction device 200, when generating vibration for delivery to the recipient.

In certain bone conduction devices, the power available to the amplifier is constant (i.e., there is a constant voltage level available at the amplifier). Therefore, in such embodiments, the MFO can be dynamically adjusted by increasing or decreasing the output compression (e.g., MFO is lowered by setting the output compression to a lower level). The net effect is lower power consumption (e.g., 3 dB lower, 50% less power consumption). Alternative strategies are possible where the available driving voltage to the amplifier is adjusted or even a different amplifier running at a different (e.g., higher or lower) voltage level is used instead.

In certain embodiments, the MFO (i.e., available battery power) may be increased in response to specific sound parameters (e.g., sound class, signal-to-noise ratio (SNR), etc.) for a predetermined period of time, until the environmental classifier 256 detects a different sound class, etc. As described further below, the determination of whether to increase the MFO, or whether to terminate the use of an increased MFO, may be further based on one or more operational parameters of the bone conduction device 200, such as a status (e.g., charge level) of the at least one battery 260.

Adjustment to one or more parameters, settings, operations, etc. of the bone conduction device 200 by the controller 258 to achieve a higher MFO is schematically represented in FIG. 2 by arrows 246 (i.e., between the controller 258 and each of the sound processing module 250, the amplifier 252, and the at least one battery 260). However, is to be appreciated that adjustments to other components/elements of bone conduction device 200 to achieve a temporarily higher MFO are also possible.

In summary, the techniques presented herein link the environment classifier 256 to the MFO control to allow for the higher outputs only in situations where the increased output would be the most beneficial to the hearing rehabilitation of the recipient. That is, an increased MFO is only used in certain sound environments (i.e., certain sound classes). In certain embodiments, the increased MFO may be used only in environments in which speech is present (i.e., "Speech" classification) or only sound environments in which speech and noise are both present (i.e., "Speech+Noise" classification). It is to be appreciated that, in certain embodiments, the environments in which the increased MFO is used could be customized based on recipient preferences. For example, a recipient who is a passionate music listener may alternatively prefer that the increased MFO is also or alternatively used when music is present (i.e., "Music" classification).

FIGS. 3A-3C are tables illustrating example average MFOs for bone conduction device 200 for different sound classes, in accordance with certain embodiments presented herein. In FIGS. 3A-3C, the MFOs are expressed in dB rel. to 1 $\mu$N. Also, the MFOs are referred to as "averages," because, in practice, the MFOs can vary across frequency for the device (i.e., different MFOs may be achievable for sound signals at 500 Hertz (Hz), than for sound signals at 4000 Hz). It is to be appreciated that the MFOs shown in FIGS. 3A-3C are merely illustrative and that bone conduction devices in accordance with embodiments presented herein may, in practice, utilize different MFOs than those shown.

FIG. 3A illustrates an example in which an increased MFO is used only when the environmental classifier 256 classifies the sounds 207 as "Speech+Noise" (i.e., both speech and noise are present in the sound environment). In this example, a standard/default MFO is used in all other sound classes (i.e., "Speech," "Noise," "Wind," "Music," and "Quiet").

FIG. 3B illustrates an example in which an increased MFO is used only when the environmental classifier 256 classifies the sounds 207 as "Speech+Noise" (i.e., both speech and noise are present in the sound environment) or when the environmental classifier 256 classifies the sounds 207 as "Music" (i.e., music is present in the sound environment). In this example, a standard/default MFO is used in all other sound classes (i.e., "Speech," "Noise," "Wind," and "Quiet").

FIG. 3C illustrates an example in which increased MFOs are used in three different sound classes. More specifically, in this example, a standard/default MFO is used in several sound classes (i.e., "Noise," "Wind," and "Quiet"). A first increased MFO is used when the environmental classifier 256 classifies the sounds 207 as "Speech," and a second increased MFO is used when the environmental classifier 256 classifies the sounds 207 as "Music." A third increased MFO is used when the environmental classifier 256 classifies the sounds 207 as "Speech+Noise."

As noted above, the MFO of the bone conduction device 200 may be increased based on the current/present sound environment of the bone conduction device. In certain embodiments, the MFO of the bone conduction device 200 may be increased based on the current/present sound environment and based one or more other parameters of the sound signals. For example, the decision regarding whether to increase the MFO of the bone conduction device 200 may also be based on the signal-to-noise ratio (SNR) of the sounds 207. In such examples, the MFO of the bone conduction device 200 is increased only in certain sound classes, and only when the SNR is below a certain threshold (i.e., when the sound classification data 238 indicates a certain class of the sound signals and specific SNRs).

FIGS. 4A-4C are tables illustrating example average MFOs for bone conduction device 200 for different sound classes and different SNRs, in accordance with certain embodiments presented herein. Similar to FIGS. 3A-3C, the MFOs in FIGS. 4A-4C are average values expressed in decibels Hearing Level (dB HL). Again, it is to be appreciated that the MFOs and SNRs shown in FIGS. 4A-4C are merely illustrative and that bone conduction devices in accordance with embodiments presented herein may, in practice, utilize different MFOs or SNR thresholds than those shown.

FIG. 4A illustrates an example in which an increased MFO is used only when the environmental classifier 256 classifies the sounds 207 as "Speech+Noise" (i.e., both speech and noise are present in the sound environment) and when the SNR of the sounds 207 are below a predetermined threshold of 6 dB. In this example, a standard/default MFO is used in all other sound classes (i.e., "Speech," "Noise," "Wind," "Music," and "Quiet"), regardless of the SNR of the associated sounds 207.

FIG. 4B illustrates an example in which an increased MFO is used when the environmental classifier 256 classifies the sounds 207 as "Speech+Noise" (i.e., both speech and noise are present in the sound environment) and when the SNR of the sounds 207 are below a predetermined threshold of 6 dB. Additionally, an increased MFO is used when the environmental classifier 256 classifies the sounds 207 as "Music" (i.e., music is present in the sound environment) and when the SNR of the sounds 207 are below a predetermined threshold of 6 dB. In this example, a standard/default MFO is used in all other sound classes (i.e., "Speech," "Noise," "Wind," and "Quiet"), regardless of the SNR of the associated sounds 207.

FIG. 3C illustrates an example in which increased MFOs are used in three different sound classes and with different SNR thresholds. More specifically, in this example, a standard/default MFO is used in several sound classes (i.e., "Noise," "Wind," and "Quiet"), regardless of the SNR of the associated sounds 207. A first increased MFO is used when the environmental classifier 256 classifies the sounds 207 as "Speech" and when the SNR of the sounds 207 are below a first predetermined threshold of 6 dB. A second increased MFO is used when the environmental classifier 256 classifies the sounds 207 as "Music" and when the SNR of the sounds 207 are below a second predetermined threshold of 9 dB. A third increased MFO is used when the environmental classifier 256 classifies the sounds 207 as "Speech+Noise" and when the SNR of the sounds 207 are below a third predetermined threshold of 10 dB.

As noted above, the use of an increased MFO improves the recipient's hearing performance. However, the use of an increased MFO is also associated with increased power consumption that could to an undesirably shorten run-time of the bone conduction device 200 and/or unexpected shutdown of the bone conduction device. Therefore, to prevent unexpected shutdowns and/or to ensure an acceptable run-time of the bone conduction device 200, the controller 258 may base the determination of whether to dynamically increase the MFO, or whether to terminate the use of an increased MFO, not only on the sound parameters (i.e., attributes of the received sounds 207, such as sound class, SNR, etc.), but also further based on one or more operational parameters of the bone conduction device 200. In certain embodiments, these operation parameters include battery information/data 264 that the controller 258 obtains from the at least one battery 260.

For example, the controller 258 may be configured to monitor a charge level of the battery 260 using the battery information 264. If the battery information 264 indicates that the charge level of the battery 260 is below a certain threshold level, the controller 258 may determine that the MFO should not be increased, or that the use of an increased MFO should be terminated, regardless of the current sound class, SNR, etc. That is, in this example, the MFO of the bone conduction device is set (i.e., either left at the default level or dynamically increased) at least based on the sound class of the sound signals and the charge level of the battery 260.

Additionally, in order to balance the need for high output with the risk of an empty battery before the end of the day, the controller 258 may base the determination of whether to increase the MFO, or whether to terminate the use of an increased MFO, not only on the sound parameters (i.e., attributes of the received sounds 207, such as sound class, SNR, etc.), but also further based on auxiliary operational data 266. This auxiliary operational data may include, for example, time-of-day (ToD) information/data (e.g., information indicating the current time), location information/data (e.g., information, such as Global Positioning System (GPS) data, indicating the current physical location of the bone conduction device), calendar information (e.g., information obtain from an electronic calendar associated with a recipient), recipient habit information (e.g., learning the recipient's normal/typical habits for different days), etc. These auxiliary operational data may be generated by the controller 258 or obtained from one or more components disposed in, or connected to (e.g., in wireless communication with), the bone conduction device 200.

In one auxiliary operational data example, the environmental classifier 256 could determine that the recipient is in a "Speech+Noise" sound environment, which could warrant an increased MFO. However, the controller 258 determines that the recipient typically goes to bed at 10:00 PM, at which time the battery 260 is set to recharge. In this example, the controller 258 also determines that the current ToD is 9:00 PM, and that the recipient is current located at his/her workplace/business. Based on this auxiliary operational data, the controller 258 determines that the recipient will likely not be going to bed at the normal time (e.g., 10:00 PM) and, as such, the life of battery 260 needs to be extended beyond that which is normal. Therefore, the controller 258 determines that, to ensure that the bone conduction device 200 continues to operate, the controller 250 precludes the use of an increased MFO even though the recipient is in a "Speech+Noise" sound environment. It is to be appreciated that this specific example is merely illustrative of one technique for using auxiliary operational data with sound classification data 238 to set the MFO (e.g., determine whether to increase the MFO, or whether to terminate the use of an increased MPO), in accordance with embodiments presented herein.

Figure 5:
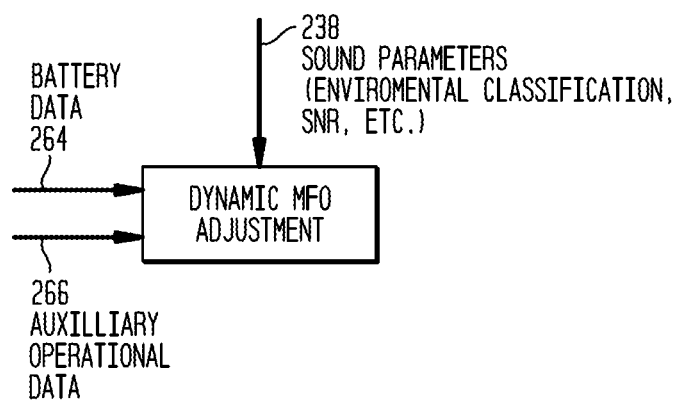
FIG. 5 is schematic diagram illustrating example inputs for a dynamic MFO adjustment process, in accordance with certain embodiments presented herein.

In certain contexts of FIG. 2, the controller 258 is described as performing a real-time or dynamic MFO adjustment process. As described above, the dynamic MFO adjustment process is based on the sound parameters 238, mainly the sound classification data, but may also be based on additional data. FIG. 5 is schematic diagram illustrating example inputs for the dynamic MFO adjustment process, including the sound parameters 238, battery data 264, and auxiliary operational data 266.

For ease of description, the embodiments of FIG. 2-5 have generally been described with reference to "average" MFOs for bone conduction device 200. However, it is to be appreciated that, in certain arrangements, the increased MFOs may not be averages, but instead the increased MFOs are selected/tailored for specific frequency ranges of sounds.

More specifically, the sound processing module 250 may include a plurality of band-pass filters, represented in FIG. 2 by dashed box 268, configured to filter the electrical signals 222 (i.e., the sounds) into a plurality of frequency components/bins, sometimes referred to as band-pass filtered signals (i.e., each band-pass filtered signal is associated with a specific frequency range of the sound signals). In such embodiments, the sound processing module 250 produces a plurality of adjusted/processed electrical signals 224 that each correspond to a specific frequency range of the received sounds 207. Each of the plurality of processed electrical signals 224 are then amplified at amplifier 252, resulting in a plurality of amplified output signals 230 that are used to drive actuator 254. In certain embodiments, the MFO of the bone conduction device 200 may be the same across the different frequencies or the MFO of the bone conduction device 200 may be set differently for different frequency bins (i.e., differently for different amplified signals 230)

For example, the speech portion of sound signals generally includes the most energy in the lower frequencies. Additionally, depending on the type of bone conduction device (e.g., electromagnetic actuator or piezoelectric actuator), most of the power loss may occur at either the higher or lower frequencies. Therefore, in order to effectively balance power consumption and increased MFO, the MFO may be set differently in the higher and/or lower different frequency regions. In the case of a bone conduction device with an electromagnetic actuator, the electromagnetic actuator will consume power mostly in the low frequencies. As such, in order to reduce power consumption, the MFO may be set lower in the low frequency regions, but higher in the high frequency regions because the power loss is not uniform across frequency.

Therefore, in summary, the MFO adjustment techniques presented herein could be implemented in a frequency-independent manner where the MFO is increased for specific sound environments, regardless of frequency. Alternatively, the MFO adjustment techniques presented herein could be implemented in a frequency-dependent manner where the MFO is increased for specific sound environments and only for specific frequencies of sounds, or the MFO can be increased differently for different frequencies in the specific sound environments. In terms of the dynamic MFO adjustment process, the frequency of the sound signals can viewed as a sound parameter 238.

FIG. 2 illustrates an embodiment in which the increased MFO (ability for extra output) is built into the device as default. In an alternative embodiment, a bone conduction device could be configured with a special "high power mode" using, for example, an auxiliary amplifier that is more powerful than the amplifier used during normal operation. It may be undesirable to use such a powerful amplifier during all operation since the auxiliary amplifier could require increased static power consumption, provide inferior sound quality in quiet environments, etc. An auxiliary amplifier is generally represented in FIG. 2 by dashed box 270. It would be appreciated that, if present, this auxiliary amplifier 270 could be activated and used to generate the amplified output signals 230 using switching and other circuitry that, for ease of illustration, have been omitted from FIG. 2.

Figure 6:
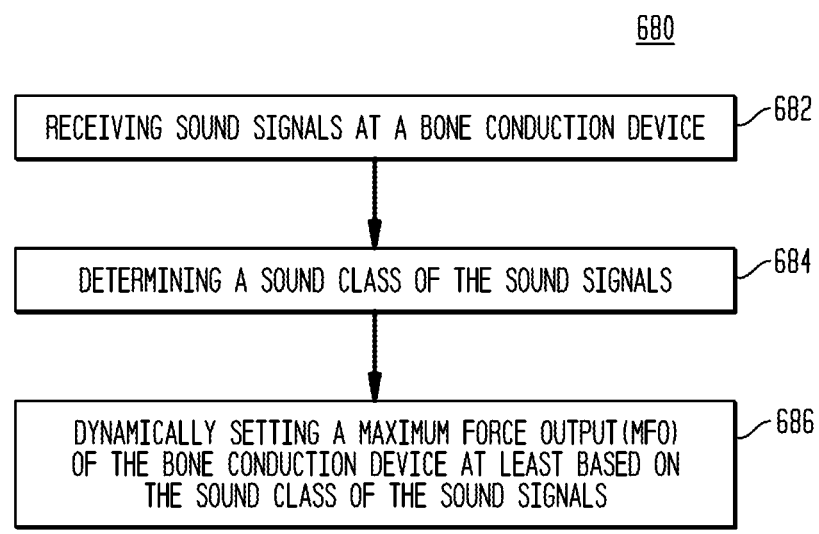
FIG. 6 is a flowchart of a method, in accordance with certain embodiments presented herein.

FIG. 6 is a flowchart of a method 680, in accordance with embodiments presented herein. Method 680 begins at 682 where sound signals (sounds) are received at one or more sound input devices of a bone conduction device. At 684, the bone conduction device determines a sound class of the sound signals. At 686, a maximum force output (MFO) of the bone conduction device is set at least based on the sound class of the sound signals.

Figure 7:
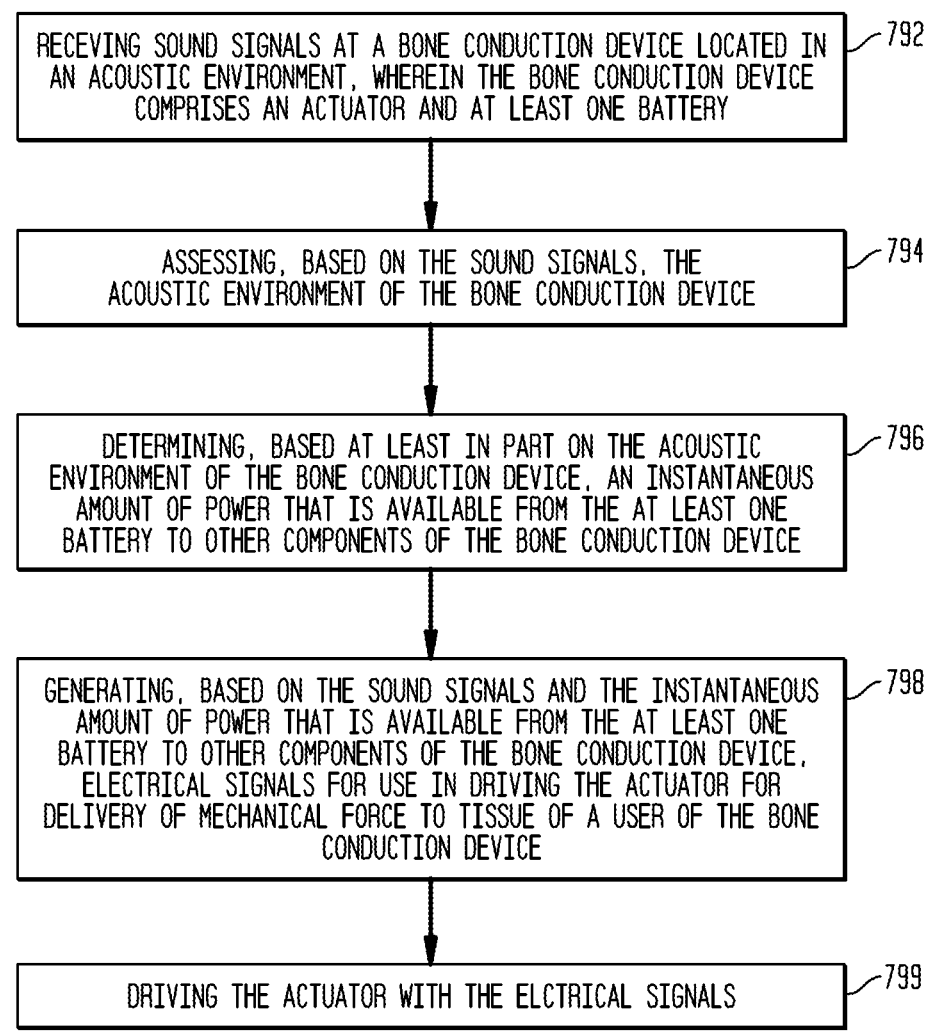
FIG. 7 is a flowchart of another method, in accordance with certain embodiments presented herein.

FIG. 7 is a flowchart of another method 790, in in accordance with embodiments presented herein. Method 790 begins at 792 where sound signals are received at a bone conduction device located in an acoustic environment, wherein the bone conduction device comprises an actuator. At 794, the acoustic environment of the bone conduction device is assessed based on the sound signals. At 796, based at least in part on the acoustic environment of the bone conduction device, an instantaneous amount of power that is available from the at least one battery to other components of the bone conduction device is determined. At 798, based on the sound signals and the instantaneous amount of power that is available from the at least one battery to other components of the bone conduction device, electrical signals for use in driving the actuator for delivery of mechanical force to tissue of a user of the bone conduction device are determined. At 799, the actuator is driven with the electrical signals.

As noted above, presented herein are bone conduction devices that are configured to use the classification (class) of the sound signals to determine whether the bone conduction device is located in a listening environment in which the recipient could benefit from a higher output. When the bone conduction device is located in a listening environment in which the recipient could benefit from a higher output, the bone conduction device is configured to generate vibration for delivery to a recipient using a higher maximum force output (MFO) than which is used in other listening environments. The techniques presented herein may be implemented in a number of different types of bone conduction devices, including percutaneous bone conduction devices, transcutaneous bone conduction devices, active transcutaneous bone conduction devices, vibrating behind-the-ear (BTE) units, vibrating headphones, etc.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method comprising:
   receiving ambient environment signals at a bone conduction device;
   determining a present sound environment based on the ambient environment signals; and
   dynamically setting a maximum force output (MFO) of the bone conduction device at least based on loudness of the present sound environment.

2. The method of claim 1, wherein determining the present sound environment comprises:
   determining a present sound class based on the ambient environment signals, and wherein dynamically setting the MFO of the bone conduction device comprises:
   dynamically setting the MFO based on the present sound class of the ambient environment signals.

3. The method of claim 2, wherein determining the present sound class of the ambient environment signals comprises:
   determining a presence of speech in the ambient environment signals; and
   classifying the ambient environment signals as speech signals, and
   wherein dynamically setting the MFO of the bone conduction device comprises:
      dynamically increasing the MFO only when the ambient environment signals are classified as speech signals.

4. The method of claim 2, wherein determining the present sound class of the ambient environment signals comprises:
   determining a presence of both speech and noise in the ambient environment signals; and
   classifying the ambient environment signals as speech and noise signals, and
   wherein dynamically setting the MFO of the bone conduction device comprises:
      dynamically increasing the MFO only when the ambient environment signals are classified as speech and noise signals.

5. The method of claim 2, wherein determining the present sound class of the ambient environment signals comprises:
   determining a presence of music in the ambient environment signals; and
   classifying the ambient environment signals as music signals, and
   wherein dynamically setting the MFO of the bone conduction device comprises:
      dynamically increasing the MFO only when the ambient environment signals are classified as music signals.

6. The method of claim 1, wherein the bone conduction device comprises at least one battery, and wherein the method further comprises:
   monitoring a charge level of the at least one battery; and
   dynamically setting the MFO of the bone conduction device based on the present sound environment and the charge level of the at least one battery.

7. The method of claim 1, further comprising:
   determining a present signal-to-noise ratio of the ambient environment signals; and
   dynamically setting the MFO of the bone conduction device based on the loudness of the present sound environment and the present signal-to-noise ratio of the ambient environment signals.

8. The method of claim 1, further comprising:
   wirelessly obtaining auxiliary operational data from the bone conduction device; and
   dynamically setting the MFO of the bone conduction device based the present sound environment and the auxiliary operational data.

9. The method of claim 8, wherein the auxiliary operational data includes at least one of time-of-day information, location information, Global Positioning System (GPS) data, calendar information, user preferences, or user habit information.

10. The method of claim 8, further comprising:
    determining current time-of-day information based on the auxiliary operational data; and
    dynamically setting the MFO of the bone conduction device based on the present sound environment and the current time-of-day information.

11. The method of claim 8, further comprising:
    determining a current location of the bone conduction device based on the auxiliary operational data; and
    dynamically setting the MFO of the bone conduction device based on the present sound environment and the current location of the bone conduction device.

12. The method of claim 1, wherein the bone conduction device includes an actuator, and the method further comprises:
    generating, based on the present sound environment of the ambient environment signals and the MFO, electrical signals for use in driving the actuator; and
    driving the actuator with the electrical signals to deliver mechanical force to tissue of a user of the bone conduction device.

13. The method of claim 12, wherein generating the electrical signals for use in driving the actuator comprises:
    automatically adjusting a gain applied to the ambient environment signals based on the present sound environment of the ambient environment signals and the MFO of the bone conduction device.

14. The method of claim 12, further comprising:
    band-pass filtering the ambient environment signals to generate band-pass filtered signals, wherein each band-pass filtered signal is associated with a specific frequency range of the ambient environment signals;
    generating, for each of a plurality of the band-pass filtered signals, corresponding electrical signals for use in driving the actuator to evoke perception of the associated frequency range of the ambient environment signals; and
    individually setting the MFO of the bone conduction device based on a frequency range associated with the corresponding band-pass filtered signal.

15. The method of claim 1, wherein determining the present sound environment comprises:
    determining whether the bone conduction device is currently in a listening environment in which a user of the bone conduction device can benefit from higher output based on a sound class of the ambient environment signals.

16. The method of claim 5, wherein dynamically setting the MFO of the bone conduction device comprises at least one of:
    dynamically increasing the MFO in response to determining that the bone conduction device is currently in a listening environment in which the user can benefit from higher output; or
    dynamically decreasing the MFO in response to determining that the bone conduction device is not currently in a listening environment in which the user can benefit from higher output.

17. The method of claim 6, wherein dynamically increasing the MFO in response to determining that the bone conduction device is currently in a listening environment in which the user can benefit from higher output comprises:

temporarily increasing the MFO for a predetermined period of time or until a different sound class is detected in the ambient environment signals.

18. The method of claim 1, wherein dynamically setting the MFO of the bone conduction device further comprises:
terminating use of an increased MFO or decreasing the MFO based on one or more of a reduction in the loudness of the present sound environment, a different sound class being detected in the ambient environment signals, a present signal-to-noise ratio of the ambient environment signals exceeding a threshold signal-to-noise ratio, a present charge level of a battery of the bone conduction device being below a threshold charge level, a change in auxiliary operational data of the bone conduction device, or expiration of a predetermined period of time.

\* \* \* \* \*